(12) United States Patent
Minnelli

(10) Patent No.: US 8,128,559 B2
(45) Date of Patent: Mar. 6, 2012

(54) TISSUE RETRACTORS

(75) Inventor: Patrick J. Minnelli, Harrison, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1021 days.

(21) Appl. No.: 11/944,796

(22) Filed: Nov. 26, 2007

(65) Prior Publication Data

US 2009/0137984 A1    May 28, 2009

(51) Int. Cl.
*A61B 1/32* (2006.01)

(52) U.S. Cl. ........ 600/206; 600/205; 600/207; 604/540; 623/17.12; 623/17.11

(58) Field of Classification Search .......... 600/205–207; 604/540; 623/17.11–17.16
See application file for complete search history.

(56) References Cited

U.S. PATENT DOCUMENTS

| | | |
|---|---|---|
| 3,745,998 A | 7/1973 | Rose |
| 3,762,404 A | 10/1973 | Sakita et al. |
| 3,897,777 A | 8/1975 | Morrison |
| 4,024,861 A | 5/1977 | Vincent |
| 4,045,830 A | 9/1977 | Loeb et al. |
| 4,213,213 A | 7/1980 | Burnett et al. |
| 4,234,982 A | 11/1980 | Bez et al. |
| 4,261,349 A | 4/1981 | Frosch et al. |
| D266,549 S | 10/1982 | Lund, III |
| 4,397,052 A | 8/1983 | Lund, III |
| 4,493,877 A | 1/1985 | Burnett et al. |
| D284,895 S | 7/1986 | Wirtz |
| 4,617,921 A | 10/1986 | Seeler |
| 4,657,003 A | 4/1987 | Wirtz |
| RE32,922 E | 5/1989 | Levin et al. |
| 4,848,364 A | 7/1989 | Bosman |
| 4,862,879 A | 9/1989 | Coombs |
| 4,885,811 A | 12/1989 | Hayes |
| 4,924,541 A | 5/1990 | Inagaki |
| 4,962,769 A | 10/1990 | Garcia |
| 4,967,431 A | 11/1990 | Hargest et al. |
| 4,984,564 A | 1/1991 | Yuen |
| 4,999,867 A | 3/1991 | Toivio et al. |
| 5,009,318 A | 4/1991 | Lepinoy |
| RE33,585 E | 5/1991 | Haber et al. |

(Continued)

FOREIGN PATENT DOCUMENTS

EP          115056 A1     8/1984

(Continued)

OTHER PUBLICATIONS

"Olympic Vac-Pac®," http://www.natus.com, retrieved Oct. 9, 2007, 2 pages.

(Continued)

*Primary Examiner* — Eduardo C Robert
*Assistant Examiner* — Christina Negrelli
(74) *Attorney, Agent, or Firm* — Nutter McClennen & Fish LLP

(57) ABSTRACT

Methods and devices are provided for performing surgical procedures using tissue retractors. In general, the methods and devices allow a surgeon to use a retractor to capture a large or small amount of tissue in the retractor and to move the retractor to relocate tissue to one or more convenient locations during a surgical procedure. The retractor can be configured from a pliable state to a substantially rigid state to hold the retractor and the tissue in a substantially fixed position during the procedure.

21 Claims, 11 Drawing Sheets

U.S. PATENT DOCUMENTS

| | | | |
|---|---|---|---|
| 5,065,464 A | 11/1991 | Blanchard et al. | |
| 5,103,517 A | 4/1992 | Krouskop | |
| 5,121,756 A | 6/1992 | Koledin | |
| 5,152,279 A | 10/1992 | Wilk | |
| 5,154,185 A | 10/1992 | Latimer et al. | |
| 5,159,921 A | 11/1992 | Hoover | |
| 5,163,942 A | 11/1992 | Rydell | |
| 5,190,033 A | 3/1993 | Johnson | |
| 5,195,505 A | 3/1993 | Josefsen | |
| 5,195,506 A | 3/1993 | Hulfish | |
| 5,218,910 A | 6/1993 | Mesmer et al. | |
| 5,240,112 A | 8/1993 | Newburger | |
| 5,248,039 A | 9/1993 | Nordlund | |
| 5,267,554 A | 12/1993 | Wilk | |
| 5,271,385 A | 12/1993 | Bailey | |
| 5,273,026 A | 12/1993 | Wilk | |
| 5,301,658 A | 4/1994 | Zhu et al. | |
| 5,309,896 A | 5/1994 | Moll et al. | |
| 5,318,586 A | 6/1994 | Ereren | |
| 5,339,801 A | 8/1994 | Poloyko et al. | |
| 5,352,237 A | 10/1994 | Rodak et al. | |
| 5,359,995 A | 11/1994 | Sewell, Jr. | |
| 5,361,752 A | 11/1994 | Moll et al. | |
| 5,362,294 A | 11/1994 | Seitzinger | |
| 5,381,788 A | 1/1995 | Matula et al. | |
| 5,391,180 A | 2/1995 | Tovey et al. | |
| 5,400,773 A | 3/1995 | Zhu et al. | |
| 5,402,772 A | 4/1995 | Moll et al. | |
| 5,425,357 A | 6/1995 | Moll et al. | |
| 5,439,476 A | 8/1995 | Frantzides | |
| 5,450,843 A | 9/1995 | Moll et al. | |
| D362,913 S | 10/1995 | Eisenberg et al. | |
| 5,454,367 A | 10/1995 | Moll et al. | |
| 5,465,711 A | 11/1995 | Moll et al. | |
| 5,468,248 A | 11/1995 | Chin et al. | |
| 5,494,165 A | 2/1996 | Detrick | |
| 5,512,037 A | 4/1996 | Russell et al. | |
| 5,514,075 A | 5/1996 | Moll et al. | |
| 5,514,157 A | 5/1996 | Nicholas et al. | |
| 5,515,975 A | 5/1996 | Jarvis et al. | |
| 5,522,790 A * | 6/1996 | Moll et al. | 600/204 |
| 5,527,264 A | 6/1996 | Moll et al. | |
| RE35,312 E | 8/1996 | Christoudias | |
| 5,549,636 A | 8/1996 | Li | |
| 5,554,101 A | 9/1996 | Matula et al. | |
| 5,562,603 A | 10/1996 | Moll et al. | |
| 5,569,165 A | 10/1996 | Chin et al. | |
| 5,575,759 A | 11/1996 | Moll et al. | |
| 5,588,951 A | 12/1996 | Zhu et al. | |
| 5,606,754 A | 3/1997 | Hand et al. | |
| 5,618,263 A | 4/1997 | Alivizatos | |
| 5,690,607 A | 11/1997 | Chin et al. | |
| 5,716,327 A | 2/1998 | Warner et al. | |
| 5,718,669 A | 2/1998 | Marble | |
| 5,738,629 A | 4/1998 | Moll et al. | |
| 5,743,851 A | 4/1998 | Moll et al. | |
| 5,758,375 A | 6/1998 | Horowitz | |
| 5,772,680 A | 6/1998 | Kieturakis et al. | |
| 5,778,470 A | 7/1998 | Haider | |
| 5,788,705 A | 8/1998 | Huddleston et al. | |
| 5,823,945 A | 10/1998 | Moll et al. | |
| 5,832,550 A | 11/1998 | Hauger et al. | |
| 5,855,207 A | 1/1999 | Moenning et al. | |
| 5,860,987 A | 1/1999 | Ratcliff et al. | |
| 5,865,728 A | 2/1999 | Moll et al. | |
| 5,865,802 A | 2/1999 | Yoon et al. | |
| 5,865,809 A | 2/1999 | Moenning et al. | |
| 5,891,069 A | 4/1999 | Moffett | |
| 5,906,205 A | 5/1999 | Hiebert | |
| 5,920,915 A | 7/1999 | Bainbridge et al. | |
| D413,258 S | 8/1999 | Voller | |
| 5,971,006 A | 10/1999 | Seigerschmidt | |
| 5,983,429 A | 11/1999 | Stacy et al. | |
| D420,846 S | 2/2000 | Voelkert et al. | |
| 6,036,640 A | 3/2000 | Corace et al. | |
| 6,036,641 A | 3/2000 | Taylor et al. | |
| 6,039,725 A | 3/2000 | Moenning et al. | |
| 6,053,829 A | 4/2000 | Conley | |
| D425,786 S | 5/2000 | Voller | |
| 6,056,768 A | 5/2000 | Cates et al. | |
| 6,063,112 A | 5/2000 | Sgro et al. | |
| 6,066,107 A | 5/2000 | Habermeyer | |
| 6,090,042 A | 7/2000 | Rullo et al. | |
| 6,109,593 A | 8/2000 | Craychee | |
| 6,126,626 A | 10/2000 | Duback et al. | |
| 6,146,401 A | 11/2000 | Yoon et al. | |
| 6,162,172 A | 12/2000 | Cosgrove et al. | |
| 6,179,852 B1 | 1/2001 | Strickland et al. | |
| 6,190,311 B1 | 2/2001 | Glines et al. | |
| 6,199,556 B1 | 3/2001 | Benetti et al. | |
| 6,226,820 B1 | 5/2001 | Navarro | |
| 6,248,119 B1 | 6/2001 | Solem et al. | |
| 6,276,365 B1 | 8/2001 | Stelzenmuller | |
| 6,308,353 B1 | 10/2001 | Van Steenburg | |
| 6,309,349 B1 | 10/2001 | Bertolero et al. | |
| 6,318,372 B1 | 11/2001 | Hiebert | |
| 6,371,964 B1 | 4/2002 | Vargas et al. | |
| 6,374,439 B2 | 4/2002 | Heimbrock et al. | |
| 6,478,029 B1 | 11/2002 | Boyd et al. | |
| 6,508,252 B1 | 1/2003 | Berg et al. | |
| 6,508,826 B2 | 1/2003 | Murphy et al. | |
| 6,517,563 B1 | 2/2003 | Paolitto et al. | |
| 6,553,995 B1 | 4/2003 | Cole et al. | |
| 6,605,037 B1 | 8/2003 | Moll et al. | |
| 6,613,055 B2 | 9/2003 | Di Emidio et al. | |
| 6,656,109 B2 | 12/2003 | DeVries et al. | |
| 6,663,562 B2 | 12/2003 | Chang | |
| 6,666,846 B1 | 12/2003 | Turovskiy et al. | |
| 6,689,103 B1 | 2/2004 | Palasis | |
| 6,712,795 B1 | 3/2004 | Cohen | |
| 6,786,898 B2 | 9/2004 | Guenst | |
| 6,830,546 B1 | 12/2004 | Chin et al. | |
| 6,890,292 B2 | 5/2005 | Kochamba et al. | |
| 6,918,393 B2 | 7/2005 | Rugfelt et al. | |
| 6,934,990 B2 | 8/2005 | Rapisarda | |
| 7,001,373 B2 | 2/2006 | Clapham et al. | |
| 7,073,508 B2 | 7/2006 | Moyers | |
| 7,125,391 B2 | 10/2006 | Joze et al. | |
| 7,147,640 B2 | 12/2006 | Huebner et al. | |
| 7,244,477 B2 | 7/2007 | Sawyer et al. | |
| 2001/0009987 A1 | 7/2001 | Moshe et al. | |
| 2001/0034527 A1 | 10/2001 | Scribner et al. | |
| 2001/0037053 A1 | 11/2001 | Bonadio et al. | |
| 2001/0051822 A1 | 12/2001 | Stack et al. | |
| 2002/0010388 A1 | 1/2002 | Taylor et al. | |
| 2002/0010389 A1 | 1/2002 | Butler et al. | |
| 2002/0022770 A1 | 2/2002 | Borsody | |
| 2002/0022845 A1 | 2/2002 | Zdeblick et al. | |
| 2002/0038128 A1 | 3/2002 | Turovkiy et al. | |
| 2002/0056460 A1 | 5/2002 | Boyd et al. | |
| 2002/0068923 A1 | 6/2002 | Caldwell et al. | |
| 2002/0069884 A1 | 6/2002 | Boyd et al. | |
| 2002/0074004 A1 | 6/2002 | Boyd et al. | |
| 2002/0077637 A1 | 6/2002 | Vargas et al. | |
| 2002/0087183 A1 | 7/2002 | Boyd et al. | |
| 2002/0091354 A1 | 7/2002 | Navia et al. | |
| 2002/0092533 A1 | 7/2002 | Boyd et al. | |
| 2002/0099270 A1 | 7/2002 | Taylor et al. | |
| 2002/0099338 A1 | 7/2002 | Young | |
| 2002/0099447 A1 | 7/2002 | Mears et al. | |
| 2002/0143343 A1 | 10/2002 | Castro | |
| 2002/0151902 A1 | 10/2002 | Riedel et al. | |
| 2002/0161391 A1 | 10/2002 | Murphy et al. | |
| 2002/0162559 A1 | 11/2002 | Crook | |
| 2002/0177874 A1 | 11/2002 | Nicholas et al. | |
| 2002/0183594 A1 | 12/2002 | Beane et al. | |
| 2002/0188301 A1 | 12/2002 | Dallara et al. | |
| 2002/0193863 A1 | 12/2002 | Rourke et al. | |
| 2003/0032967 A1 | 2/2003 | Park et al. | |
| 2003/0040717 A1 | 2/2003 | Saulenas et al. | |
| 2003/0055319 A1 | 3/2003 | Chang | |
| 2003/0062051 A1 | 4/2003 | Rambo | |
| 2003/0065351 A1 | 4/2003 | Hess et al. | |
| 2003/0074015 A1 | 4/2003 | Nakao | |
| 2003/0078478 A1 | 4/2003 | Bonadio et al. | |
| 2003/0083621 A1 | 5/2003 | Shaw et al. | |
| 2003/0105486 A1 | 6/2003 | Murphy et al. | |

| | | | |
|---|---|---|---|
| 2003/0176771 A1 | 9/2003 | Pulford et al. | |
| 2003/0187376 A1 | 10/2003 | Rambo | |
| 2003/0191478 A1 | 10/2003 | Kortenbach et al. | |
| 2003/0192553 A1 | 10/2003 | Rambo | |
| 2003/0195519 A1 | 10/2003 | Zdeblick et al. | |
| 2003/0195544 A1 | 10/2003 | Hess et al. | |
| 2004/0034351 A1 | 2/2004 | Sherman et al. | |
| 2004/0049100 A1 | 3/2004 | Butler et al. | |
| 2004/0068276 A1 | 4/2004 | Golden et al. | |
| 2004/0073090 A1 | 4/2004 | Butler et al. | |
| 2004/0082923 A1 | 4/2004 | Field | |
| 2004/0092796 A1 | 5/2004 | Butler et al. | |
| 2004/0097793 A1 | 5/2004 | Butler et al. | |
| 2004/0097949 A1 | 5/2004 | Bonutti | |
| 2004/0133222 A1 | 7/2004 | Tran et al. | |
| 2004/0138526 A1 | 7/2004 | Guenst | |
| 2004/0143167 A1 | 7/2004 | Branch et al. | |
| 2004/0147812 A1 | 7/2004 | Hamel | |
| 2004/0176665 A1 | 9/2004 | Branch et al. | |
| 2004/0199052 A1 | 10/2004 | Banik et al. | |
| 2004/0254426 A1 | 12/2004 | Wenchell | |
| 2004/0260153 A1 | 12/2004 | Pulford et al. | |
| 2004/0267303 A1 | 12/2004 | Guenst | |
| 2007/0027545 A1* | 2/2007 | Carls et al. | 623/17.12 |
| 2009/0137877 A1 | 5/2009 | Minnelli et al. | |

FOREIGN PATENT DOCUMENTS

| | | |
|---|---|---|
| EP | 176452 A1 | 4/1986 |
| EP | 196990 A1 | 10/1986 |
| EP | 288879 A2 | 11/1988 |
| EP | 353916 A1 | 2/1990 |
| EP | 384583 A1 | 8/1990 |
| EP | 410561 A1 | 1/1991 |
| EP | 449663 | 10/1991 |
| EP | 469524 A1 | 2/1992 |
| EP | 499457 A1 | 8/1992 |
| EP | 545540 A1 | 6/1993 |
| EP | 568296 A1 | 11/1993 |
| EP | 586516 A1 | 3/1994 |
| EP | 586555 A1 | 3/1994 |
| EP | 602757 A2 | 6/1994 |
| EP | 610099 | 8/1994 |
| EP | 613351 A1 | 9/1994 |
| EP | 613659 A1 | 9/1994 |
| EP | 630211 A1 | 12/1994 |
| EP | 636036 A1 | 2/1995 |
| EP | 654247 A1 | 5/1995 |
| EP | 698374 A2 | 2/1996 |
| EP | 712306 A1 | 5/1996 |
| EP | 720446 A1 | 7/1996 |
| EP | 734231 A1 | 10/1996 |
| EP | 746350 A1 | 12/1996 |
| EP | 791330 A2 | 8/1997 |
| EP | 810843 A1 | 12/1997 |
| EP | 835639 A2 | 4/1998 |
| EP | 836811 A2 | 4/1998 |
| EP | 843987 A1 | 5/1998 |
| EP | 875260 A2 | 11/1998 |
| EP | 888750 A1 | 1/1999 |
| EP | 906064 A1 | 4/1999 |
| EP | 956060 A1 | 11/1999 |
| EP | 981302 A1 | 3/2000 |
| EP | 1125552 A1 | 8/2001 |
| EP | 1177772 A1 | 2/2002 |
| EP | 1208865 A2 | 5/2002 |
| EP | 1312318 A1 | 5/2003 |
| EP | 1472982 A2 | 11/2004 |
| EP | 1611862 A1 | 1/2006 |
| WO | WO-9105200 A1 | 4/1991 |
| WO | WO-9106261 A1 | 5/1991 |
| WO | WO-9219294 A1 | 11/1992 |
| WO | WO-9221292 A2 | 12/1992 |
| WO | WO-9221294 A1 | 12/1992 |
| WO | WO-9309709 A1 | 5/1993 |
| WO | WO-9309722 A1 | 5/1993 |
| WO | WO-9311811 A1 | 6/1993 |
| WO | WO-9317625 A1 | 9/1993 |
| WO | WO-9320755 A1 | 10/1993 |
| WO | WO-9320866 A1 | 10/1993 |
| WO | WO-9322973 A1 | 11/1993 |
| WO | WO-9325148 A1 | 12/1993 |
| WO | WO-9403114 A1 | 2/1994 |
| WO | WO-9416630 A1 | 8/1994 |
| WO | WO-9422384 A1 | 10/1994 |
| WO | WO-9424947 A1 | 11/1994 |
| WO | WO-9501193 A1 | 1/1995 |
| WO | WO-9502988 A2 | 2/1995 |
| WO | WO-9508952 A1 | 4/1995 |
| WO | WO-9515723 A1 | 6/1995 |
| WO | WO-9522289 A2 | 8/1995 |
| WO | WO-9602195 A1 | 2/1996 |
| WO | WO-9610430 A2 | 4/1996 |
| WO | WO-9620749 A1 | 7/1996 |
| WO | WO-9624291 A1 | 8/1996 |
| WO | WO-9640354 A1 | 12/1996 |
| WO | WO-9700049 A1 | 1/1997 |
| WO | WO-9707741 A1 | 3/1997 |
| WO | WO-9707742 A1 | 3/1997 |
| WO | WO-9725940 A1 | 7/1997 |
| WO | WO-9730666 A2 | 8/1997 |
| WO | WO-9732514 A2 | 9/1997 |
| WO | WO-9742893 A1 | 11/1997 |
| WO | WO-9802102 A2 | 1/1998 |
| WO | WO-9817208 A2 | 4/1998 |
| WO | WO-9824374 A1 | 6/1998 |
| WO | WO-9827869 A1 | 7/1998 |
| WO | WO-9834569 A1 | 8/1998 |
| WO | WO-9835714 A1 | 8/1998 |
| WO | WO-9848724 A1 | 11/1998 |
| WO | WO-9855029 A1 | 12/1998 |
| WO | WO-9903416 A1 | 1/1999 |
| WO | WO-9905976 A1 | 2/1999 |
| WO | WO-9909892 A1 | 3/1999 |
| WO | WO-9912477 A1 | 3/1999 |
| WO | WO-9912481 A1 | 3/1999 |
| WO | WO-9915226 A1 | 4/1999 |
| WO | WO-9921484 A2 | 5/1999 |
| WO | WO-9937345 A1 | 7/1999 |
| WO | WO-9938440 A1 | 8/1999 |
| WO | WO-9952445 A1 | 10/1999 |
| WO | WO-9952448 A1 | 10/1999 |
| WO | WO-9962457 A1 | 12/1999 |
| WO | WO-0001293 A2 | 1/2000 |
| WO | WO-0009024 A1 | 2/2000 |
| WO | WO-0010466 A1 | 3/2000 |
| WO | WO-0024326 A2 | 5/2000 |
| WO | WO-0032116 A2 | 6/2000 |
| WO | WO-0054675 A1 | 9/2000 |
| WO | WO-0061011 A1 | 10/2000 |
| WO | WO-0061035 A1 | 10/2000 |
| WO | WO-0062845 A1 | 10/2000 |
| WO | WO-0069346 A1 | 11/2000 |
| WO | WO-0069368 A2 | 11/2000 |
| WO | WO-0071033 A1 | 11/2000 |
| WO | WO-0078246 A2 | 12/2000 |
| WO | WO-0108581 A2 | 2/2001 |
| WO | WO-0124682 A2 | 4/2001 |
| WO | WO-0126558 A1 | 4/2001 |
| WO | WO-0126559 A1 | 4/2001 |
| WO | WO-0134228 A1 | 5/2001 |
| WO | WO-0160262 A1 | 8/2001 |
| WO | WO-0209591 A2 | 2/2002 |
| WO | WO-0222053 A2 | 3/2002 |
| WO | WO-0239880 A2 | 5/2002 |
| WO | WO-02058993 A1 | 8/2002 |
| WO | WO-02076308 A2 | 10/2002 |
| WO | WO-02087652 A2 | 11/2002 |
| WO | WO-03000142 A2 | 1/2003 |
| WO | WO-03015855 A1 | 2/2003 |
| WO | WO-03028523 A2 | 4/2003 |
| WO | WO-03070085 A2 | 8/2003 |
| WO | WO-03077726 A2 | 9/2003 |
| WO | WO-03090644 A1 | 11/2003 |
| WO | WO-03094744 A1 | 11/2003 |
| WO | WO-03094754 A1 | 11/2003 |
| WO | WO-03096851 A1 | 11/2003 |
| WO | WO-03101314 A1 | 12/2003 |
| WO | WO-03103548 A1 | 12/2003 |

| | | |
|---|---|---|
| WO | WO-2004011037 A2 | 2/2004 |
| WO | WO-2004016186 A1 | 2/2004 |
| WO | WO-2004016299 A2 | 2/2004 |
| WO | WO-2004026153 A1 | 4/2004 |
| WO | WO-2004026371 A2 | 4/2004 |
| WO | WO-2004030547 A1 | 4/2004 |
| WO | WO-2004041148 A1 | 5/2004 |
| WO | WO-2004050138 A2 | 6/2004 |
| WO | WO-2004052178 A2 | 6/2004 |
| WO | WO-2004071312 A1 | 8/2004 |
| WO | WO-2004075741 A2 | 9/2004 |
| WO | WO-2004096012 A2 | 11/2004 |
| WO | WO-2004096060 A2 | 11/2004 |
| WO | WO-2004098395 A1 | 11/2004 |
| WO | WO-2004103161 A2 | 12/2004 |
| WO | WO-2004110263 | 12/2004 |
| WO | WO-2005116512 A1 | 12/2005 |
| WO | WO-2007060000 A2 | 5/2007 |

OTHER PUBLICATIONS

"Olympic Vac-Pac®," http://www.olymed.net, retrieved Oct. 9, 2007, 2 pages.

International Search Report & Written Opinion, PCT/US2008/0884470, Mailed Jun. 30, 2009, 14 pages.

International Preliminary Report on Patentability, PCT/US2008/0884470, Mailed Jun. 10, 2010, 10 pages.

* cited by examiner

TISSUE RETRACTORS

FIELD OF THE INVENTION

The present invention relates to methods and devices for manipulating tissue.

BACKGROUND OF THE INVENTION

During certain surgical procedures, body tissue such as organs can obstruct an area a surgeon needs accessible for surgery. Relocating the tissue during all or part of the procedure can allow a surgeon to access an otherwise obstructed part of the body. The tissue may also need to be relocated to reduce chances of it being damaged as work is being done on another, nearby part of the body.

Visceral retractors have been developed that allow some movement of tissue in a body cavity during a surgical procedure. For example, a visceral retractor may be inserted into the body through an incision, and it can be used to push tissue aside to provide access to an underlying area. Current retractors include a rigid fan-type design, a spoon or fork-like device, or an inflatable bladder. While such visceral retractors can move tissue, they typically move small amounts of tissue and are difficult or impossible to keep in a fixed position during use without constant human interaction.

Accordingly, there remains a need for improved methods and devices for manipulating tissue.

SUMMARY OF THE INVENTION

The present invention generally provides tissue retractor devices as well as methods for performing various procedures using tissue retractors. In one embodiment, an implantable tissue retractor device is provided and includes a tissue retractor formed of a flexible biocompatible material defining an internal cavity having a plurality of granules, which can be composed of a biocompatible material. The tissue retractor has a first state in which it is selectively conformable to a target tissue in a body cavity in a desired configuration and a second state in which it is substantially rigid and in a substantially fixed conformation.

The tissue retractor can have a variety of configurations, but in one embodiment, at least one tab can be on the outside surface of the tissue retractor. In another embodiment, a valve can be located on an outer surface of the tissue retractor and can be in fluid communication with the internal cavity such that the valve can selectively allow passage of fluid therethrough. The tissue retractor can be configured from the first state to the second state by removing fluid from within the internal cavity. In some embodiments, the internal cavity can be formed along a perimeter of the tissue retractor with a mesh material disposed within a central opening defined by the internal cavity.

In other embodiments, the tissue retractor can also include at least one conduit in fluid communication with the internal cavity such that fluid can be removed from the internal cavity through the at least one conduit. The conduit can be detachable from the tissue retractor. Additionally, a valve in fluid communication with the internal cavity can be coupled to the conduit such that when the valve is coupled to the conduit and the valve is in an open position, the conduit is in fluid communication with the internal cavity.

In another embodiment, an implantable tissue retractor device includes an implantable, biocompatible retractor body having an internal cavity. The internal cavity can, in some embodiments, extend around at least a portion of a perimeter of the retractor body, which may include a flexible fabric disposed within the perimeter of the retractor body. The tissue retractor can have a default non-rigid state and can be disposed in a body cavity. Constrictable material can be disposed in the internal cavity, and constricting the material can cause the retractor body to have a rigid state in which the retractor body is effective to support tissue in a body cavity in a selected substantially fixed position. The material can include a viscous fluid responsive to a magnetic field, or, alternatively, biocompatible granules.

In other aspects, a surgical method is provided that in one embodiment includes inserting a conformable tissue retractor into a body cavity in a first orientation, wherein the retractor has an internal cavity comprising a plurality of granules. Tissue can be positioned with respect to the tissue retractor in a desired conformation that is different than the first orientation such that the tissue retractor supports a target tissue. The method can further include evacuating a fluid from within the internal cavity such that the granules compact together to maintain the tissue retractor in the desired conformation such that it is able to hold the target tissue in a substantially fixed position. In one embodiment, evacuating a fluid from within the internal cavity can include applying a vacuum force to withdraw fluid from within the internal cavity. The method can also include removing the vacuum force and allowing fluid to re-enter the internal cavity to enable the target tissue to be released from the substantially fixed position. Removing the vacuum force can include opening a valve on the tissue retractor that is in fluid communication with the internal cavity.

In another embodiment, a surgical method can include introducing a pliable retractor into a body cavity in a first conformable configuration. The retractor can be configured in a rigid state in a desired orientation with respect to a target tissue such that the retractor is effective to support tissue in the body cavity in a substantially fixed position. In some embodiments, configuring the retractor in the rigid state includes introducing a magnetic field to the internal cavity, while in other embodiments it includes introducing a vacuum to the internal cavity. In other embodiments, the method can include decompressing material disposed in the internal cavity such that the retractor can change from the rigid state to a non-rigid state. Decompressing the material can include removing a vacuum from the internal cavity. The method can further include positioning the retractor in the body cavity such that the retractor supports tissue before configuring the retractor in the rigid state.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
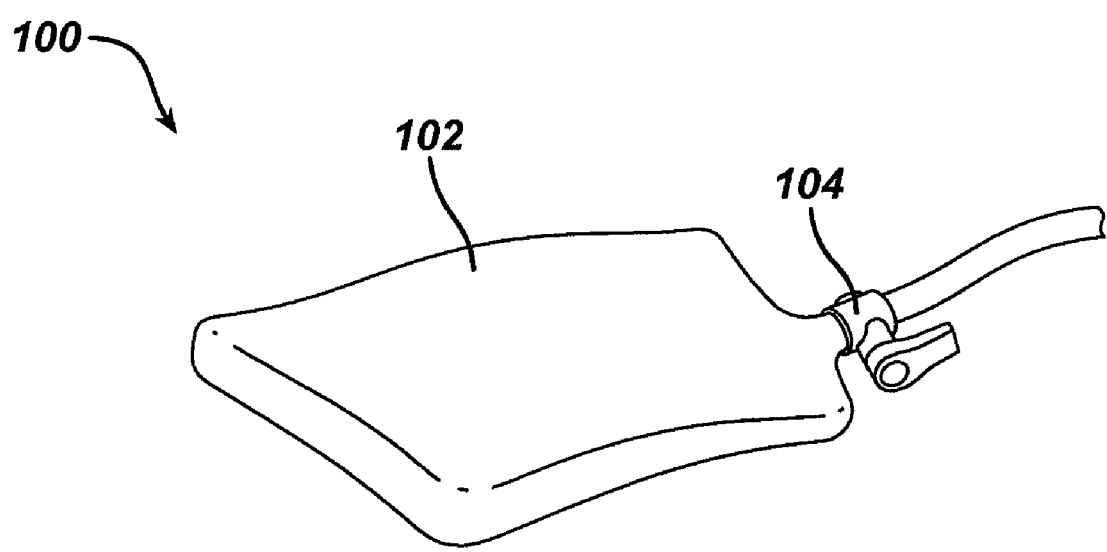
FIG. 1 is a schematic diagram of an embodiment of a retractor having an internal cavity.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for performing surgical procedures using tissue retractors. In general, the methods and devices allow a surgeon to use a retractor to capture a large or small amount of tissue in the retractor, to move the retractor to relocate tissue to one or more convenient locations during a surgical procedure, and to configure the retractor from a pliable state to a substantially rigid state to hold the retractor and the tissue in a selected substantially fixed position during the procedure. The pliable nature of the retractor can allow the retractor to be moveable between an open position, in which the retractor can support tissue, and a closed position, in which the retractor can be rolled, folded, or otherwise compressed in size and fit through a relatively small port, e.g., a trocar or an incision in a tissue wall. Once the retractor is inside the body, the need to repeatedly position tissue during a procedure can be reduced because more than a small amount of tissue can be held in the retractor and moved at a time. The pliable nature of the retractor can allow more freedom of movement in positioning the retractor within the body and moving the tissue rather than a retractor made of non-pliable material, such as metal. Additionally, holding and moving tissue in a retractor that can be oriented in pliable and substantially rigid states can reduce the chances of tissue slipping or sliding away from the retractor, a common occurrence when using non-pliable retractors. This also reduces the need for tissue reengaging and repositioning. Furthermore, the retractor can be molded to the shape of tissue, thereby increasing the amount of tissue area being supported by the retractor and reducing the chances of the tissue from slipping or sliding away from a desired position. Another feature of the retractor is that it can be anchored and maintain tissue in a desired location without the need for a surgeon to constantly hold and manipulate the retractor.

A person skilled in the art will appreciate that the devices disclosed herein can be used in numerous surgical procedures (including endoscopic, laparoscopic and hand-assisted laparoscopic surgery ("HALS") procedures), and in connection with numerous body cavities and body tissues. For example, the devices can be used in procedures that take place in the abdominal, thoracic, pelvic, and abdominopelvic cavities, and they can be used to move any tissue, including organs such as the bowel, small intestine, stomach, liver, uterus, etc. The devices can be introduced into the body in any way in any of the procedures, such as through an incision or percutaneously through an access device, such as a trocar or an endoscopic device.

A person skilled in the art will also appreciate that the particular configuration and materials of the retractor can vary depending on factors such as the type of procedure being performed and the type of tissue to be moved or relocated. The retractor can have any shape with any number of sides, curves, and cut-out shapes, e.g., rectangular (including square), elliptical (including circular), triangular, hexagonal, trapezoidal, T-shaped, U-shaped, etc. The retractor can also be made from any flexible material appropriate for surgical use and can include zero, one, or more structural elements, e.g., tabs, compressible chambers, grasping elements, etc. Structural elements coupled to the retractor can be of any number and configuration on the fabric.

FIG. 1 illustrates one embodiment of a retractor 100 having a body 102 that can hold tissue during a surgical procedure. The substantially rectangular shaped retractor body 102 as shown is formed of a flexible biocompatible material and is in a pliable state. The retractor body 102 defines at least one internal cavity. At least one valve 104 located on an outer surface of the retractor body 102 can be in fluid communication with the internal cavity and selectively allow passage of fluid therethrough. Once inside the body and in the pliable state, the retractor body 102 can be manipulated into a configuration to receive, hold, move, and release tissue. From such a configuration, the retractor body 102 can be conformed from the pliable state to a substantially rigid state by manipulating material disposed in the internal cavity, as further described below. The retractor body 102 can thereby support tissue in a selected substantially fixed position within the body. Additionally, while still inside the body, the retractor body 102 can be released from the substantially fixed position by again manipulating the material in the internal cavity and changing the retractor body 102 from the substantially rigid state to the pliable state.

The retractor body 102 can have a variety of configurations that allow the retractor body 102 to hold tissue and temporarily move tissue to another location during a surgical procedure. In the illustrated embodiment, the retractor body 102 has a substantially rectangular shape, although the retractor body 102 can have any shape as mentioned above. The retractor body 102 can also have a two dimensional shape when in an open configuration as shown, but in other embodiments the retractor body 102 can have a third dimension. For example, the retractor body's 102 shape in an open position can be cone-shaped, domed, elliptical (similar to a parachute), or prism-shaped with one or more sides of the prism missing so as to allow tissue to be held in the retractor body 102.

The retractor body 102 can also have a variety of sizes, and different sizes of the retractor body 102 may be appropriate for relocation of different types of tissue, e.g., a larger body for moving the liver than for moving the stomach. In one embodiment, the retractor body 102 can have dimensions that allow it to fit inside a commercially available cannula so that the retractor body 102 can be introduced into a body through the cannula.

The valve 104 attached to the retractor body 102 can also have any structure. For example, the valve 104 can include a stopcock (as illustrated in FIG. 1), a connection port, a check valve, and other similar structures. The valve 104 can have any shape, such as elliptical (including circular), and be of any size. The valve 104 can be configured to have a shape and size compatible to couple with commercially available fluid conduits such as tubes, hoses, and pumps, as further discussed below, thereby allowing fluid disposed in the retractor body's internal cavity to be introduced and/or evacuated through the valve 104. In use, the valve 104 in a closed position can maintain the retractor body 102 as a closed pouch able to hold its shape and internal pressure, e.g., by preventing fluid passage to and/or from the retractor body 102. In contrast, the valve 104 in an open position can allow the retractor body 102 to change shape and/or internal pressure.

Any number of valves 104 (including zero, in some embodiments) can be coupled to the retractor body 102 in any configuration, and the valve 104 can be coupled to the retractor body 102 at any point or points along the retractor body's perimeter or elsewhere on its surface. If the retractor 100 includes more than one internal cavity, each of the internal cavities can have a dedicated valve 104. Furthermore, the valve 104 can be used for both fluid introduction and evacuation, as in the embodiment shown in FIG. 1, or the retractor 100 can include two valves 104, one for fluid introduction and one for fluid evacuation.

The valve 104 can be mated to the retractor body 102, or it can be integrally formed with the retractor body 102. For example, FIG. 1 illustrates the valve 104 mated to the retractor body 102. The valve 104 is permanently coupled to the retractor body 102, but in other embodiments, the valve 104 can be removable.

The retractor body 102 and the valve 104 can each be made from any type of and any combination of biocompatible material appropriate for use in a body, such as mesh (braided or unbraided), fiber (natural or synthetic), gauze-like cloth, a polymer, biocompatible metal, and other similar types of material. The retractor body 102 can be made from two or more layers of material, e.g., a synthetic fiber outside surface that can come into contact with tissue and a polymerized inside surface defining the internal cavity. Moreover, the retractor body 102 can be fluid pervious or impervious, and the material can be treated to increase or decrease its frictional interaction with tissue. It is understood, of course, that portions of the retractor body 102 that define an internal cavity should be made of a fluid impervious material. The retractor body 102 can also include structural elements such as grasping elements, described further below. The retractor body 102 is made from a flexible, elastic material, while the valve 104 can be made from a flexible, elastic or non-flexible, non-elastic material.

Figure 2:
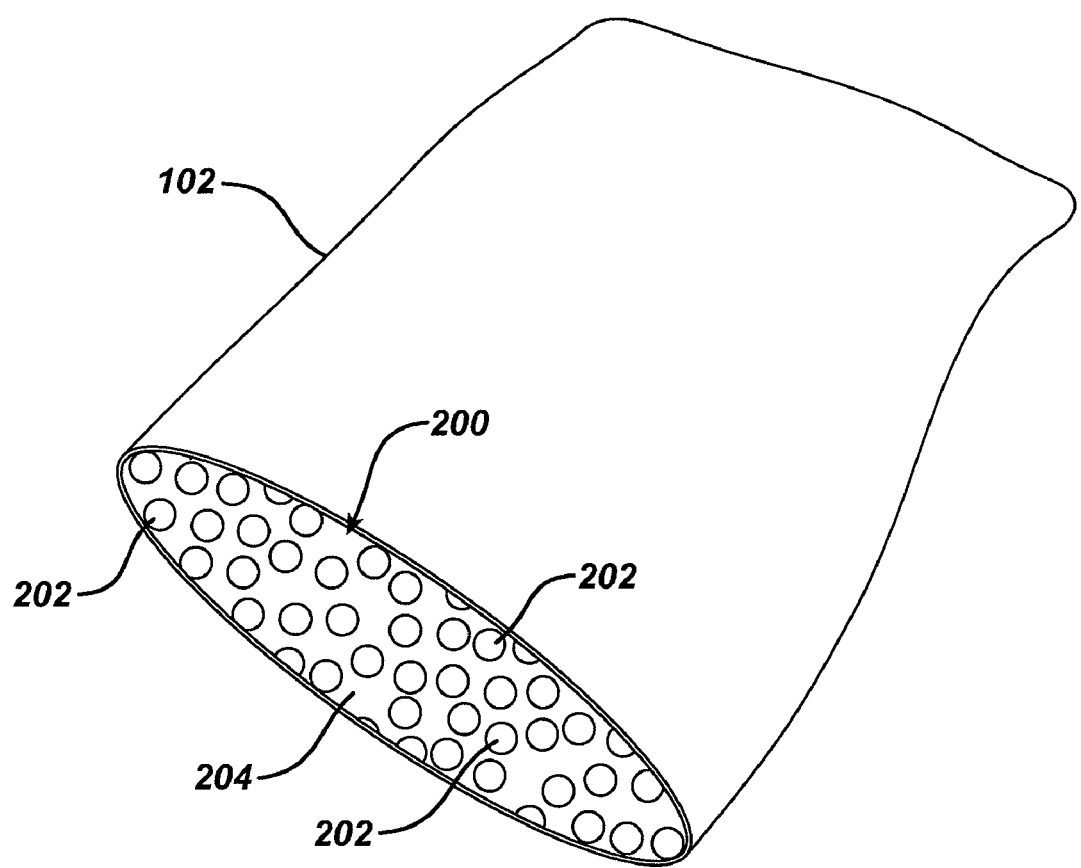
FIG. 2 is a cross-sectional view of the retractor of FIG. 1 in a pliable state.

As indicated above, the retractor body 102 defines an internal cavity 200, illustrated in FIG. 2. In this embodiment, the internal cavity 200 is shown having a substantially rectangular shape, but the internal cavity 200 can have any shape as well as any size. If the internal cavity 200 includes more than one chamber and/or one or more channels putting multiple chambers in fluid communication, each chamber and each channel can have any size, different or the same from any other chamber or channel included in the internal cavity 200.

The internal cavity 200 can have a variety of configurations. For example, the internal cavity 200 can be formed in the retractor body 102 as a defined space, e.g., two pieces of fabric or other material mated together as discrete portions to create one or more cavities therein. The illustrated cavity 200 has one chamber, but the retractor body 102 can include any number of internal cavities including two or more cavities connected by any number of channels (including zero channels) through which material disposed in the internal cavity 200 can flow. In use, fluid can be introduced into and/or evacuated from the internal cavity 200 through the valve 104, and fluid can travel to and/or from one or more other internal cavities, if present, via any number of channels. Alternatively, the internal cavity 200 can include any number of unconnected cavities, and fluid can be separately introduced into each cavity to allow each cavity to be manipulated in a selected way.

Figure 3:
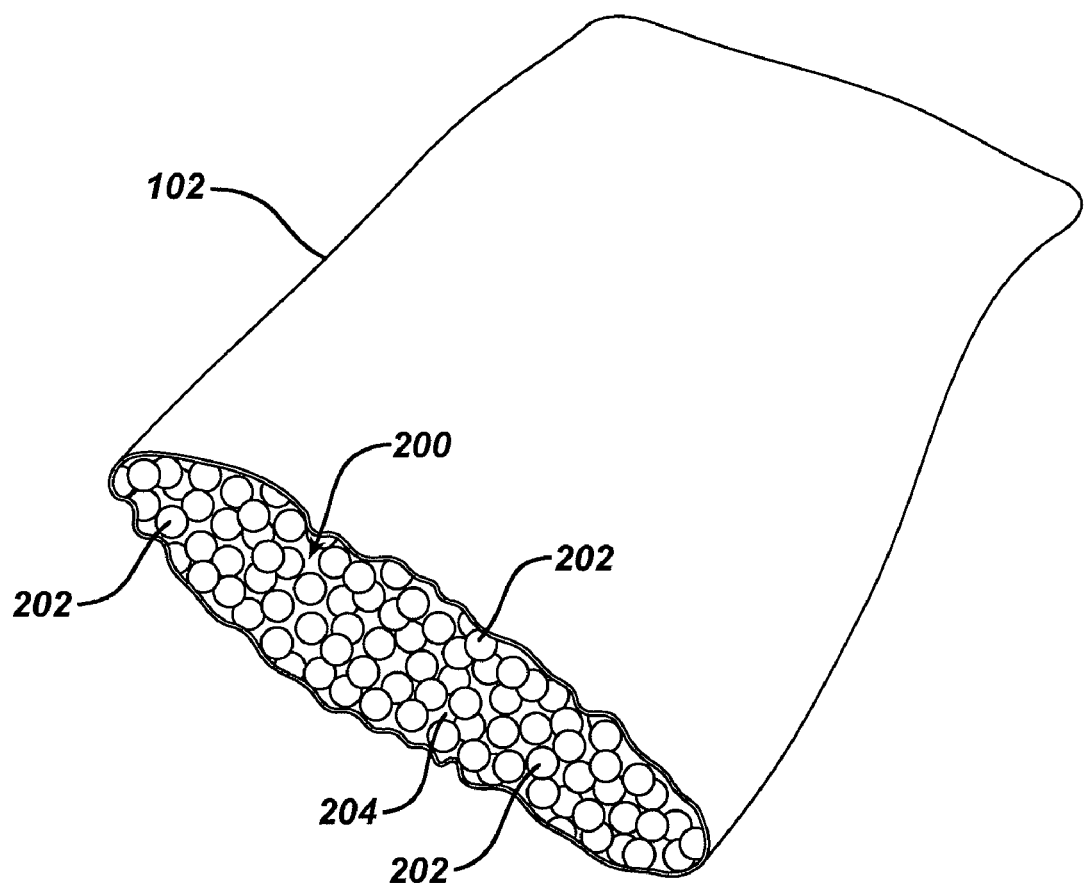
FIG. 3 is a cross-sectional view of the retractor of FIG. 1 in a substantially rigid state.

Constrictable material, such as a plurality of granules 202 and/or a fluid 204, can be disposed in the internal cavity 200. The retractor 100 has a pliable state (shown in FIG. 2) where the granules 202 and/or the fluid 204 disposed in the internal cavity 200 allow the retractor body 102 to be selectively comformable to a target tissue in a body cavity, as described further below. The retractor 100 also has a substantially rigid state (shown in FIG. 3), also described further below, where the physical state of the granules 202 and/or the fluid 204 disposed in the internal cavity 200 has been changed and the granules 202 have been constricted or compacted, such as by removing at least a portion of the fluid 204 from the internal cavity 200. When in the substantially rigid state, the retractor 100 in use can be held in a substantially fixed conformation such that it can support tissue in a selected substantially fixed position. The retractor 100 can be introduced to a body cavity in either the pliable state (typically the retractor's default state) or the substantially rigid state and can change between the states any number of times. When the retractor 100 is in the pliable state, it can maintain a substantially flat yet pliable configuration allowing the retractor 100 to be folded or otherwise compressed for easy introduction into, or removal out of, a body cavity.

The plurality of granules 202 are shown as substantially spherical beads in this embodiment, but the granules 202 can be of any type and have any shape. For example, the granules 202 can have a two-dimensional or three-dimensional ovular, rectangular, cylindrical, rod, or other similar shape. The granules 202 can also have any size, although the granules 202 are typically of a size that prevents their passage through the valve 104. If the internal cavity 200 includes two or more chambers, the granules 202 can be restricted from passage between chambers, such as by the absence of chamber-connecting channel(s) or by the presence of vent-like channel(s) that allow passage of the fluid 204 but not passage of the granules 202 between the chambers. Such restricted passage between chambers can provide for more even distribution of the granules 202 throughout the internal cavity 200. While the granules 202 disposed in the internal cavity 200 can have the same shape and size, any number of the granules 202 can differ in shape and/or size from other granules 202 disposed in the internal cavity 200. Any number of the granules 202 can be disposed in the internal cavity 200. The granules 202 can be made from any type of material, typically a biocompatible material appropriate for use in a body to minimize patient harm in the uncommon occurrence of retractor body rupture. For example, the granules 202 can be composed of medical grade polymers such as polyethylene, polypropylene, polyurethane foam or an organic compound, such as sugar. The granules 202 can be elastic or non-elastic.

The fluid 204 is shown as air in FIG. 2, but the fluid 204 can include any type of gas or liquid (e.g., saline, a viscous fluid, etc.). The type of fluid 204 disposed in the internal cavity 200 is compatible with the valve 104 such that the fluid 204 can be introduced and/or evacuated through the valve 104. The fluid 204 is typically a biocompatible material appropriate for use in a body (although it typically does not come into contact with a body) and a material compatible with the granules' material. The amount of fluid 204 disposed in the internal cavity 200 can vary, but the amount of fluid 204 disposed in the internal cavity 200 when the retractor 100 is in the pliable state is more than when the retractor 100 in the substantially rigid state. In some embodiments, such as one further described below, the fluid 204 includes a viscous fluid responsive to a magnetic field and the granules 202 need not be present.

Figure 4:
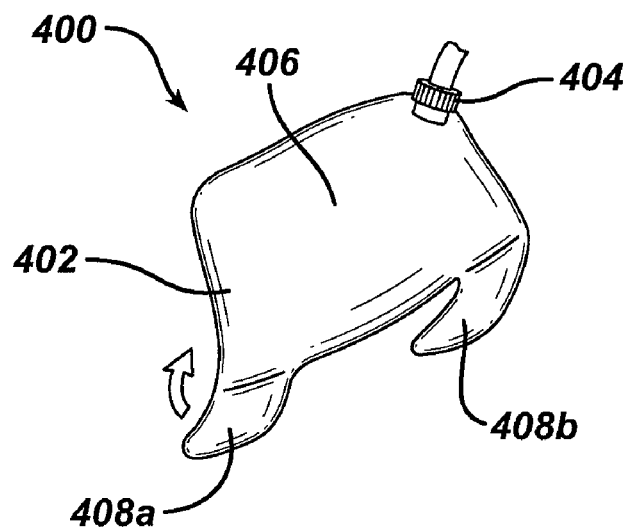
FIG. 4 is a schematic diagram of an embodiment of a retractor having an internal cavity and tabs.

FIG. 4 illustrates another embodiment of a retractor 400 having a body 402 that can hold tissue during a surgical procedure. The retractor 400 is similar to the retractor 100 of FIG. 1 and includes a retractor body 402 defining an internal cavity with fluid and/or granules disposed therein. The retractor 400 also includes a valve 404 mated to one corner of the retractor body 402. The retractor body 402, the valve 404 (shown in this embodiment as a connection port), the internal cavity, the granules, and the fluid are similar to those described with reference to similarly named elements included in FIGS. 1-3, and the retractor 400 can include variations as described herein for various retractors.

The retractor body 402 has a central body 406 and two tabs 408a, 408b extending from the central body 406. The retractor body's internal cavity can extend between the central body 406 and the tabs 408a, 408b as shown in FIG. 4, or the internal cavity can be separated into one or more chambers, e.g., a chamber for each of the central body 406 and the tabs 408a, 408b. The tabs 408a, 408b can have any shape (same or different from the central body 406) and in this embodiment are substantially rectangular. The tabs 408a, 408b can also have any size, although the tabs 408a, 408b are typically each smaller in area than the central body 406. The tabs 408a, 408b can each be folded in one or more directions, such as backwards as shown by the directional arrow for the left tab 408a, to aid in conforming the retractor 400 to a target tissue and/or to increase stability of the retractor 400 in its substantially rigid state. The retractor body 402 can include scored, weakened, and/or thinned material at a junction between the central body 406 and one or more of the tabs 408a, 408b to help facilitate tab folding. Although not illustrated, it is understood that one or more of the tabs 408a, 408b can have one or more apertures (e.g., grommets) to assist in securing the retractor 400 in place, such as by way of sutures.

Figure 5:
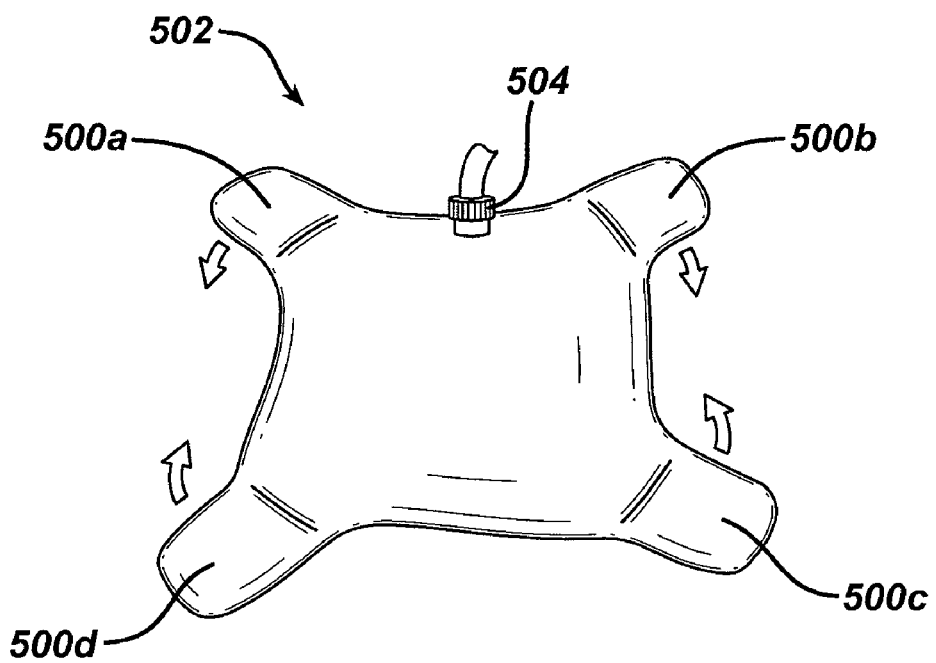
FIG. 5 is a schematic diagram of another embodiment of a retractor having an internal cavity and tabs.
Figure 6:
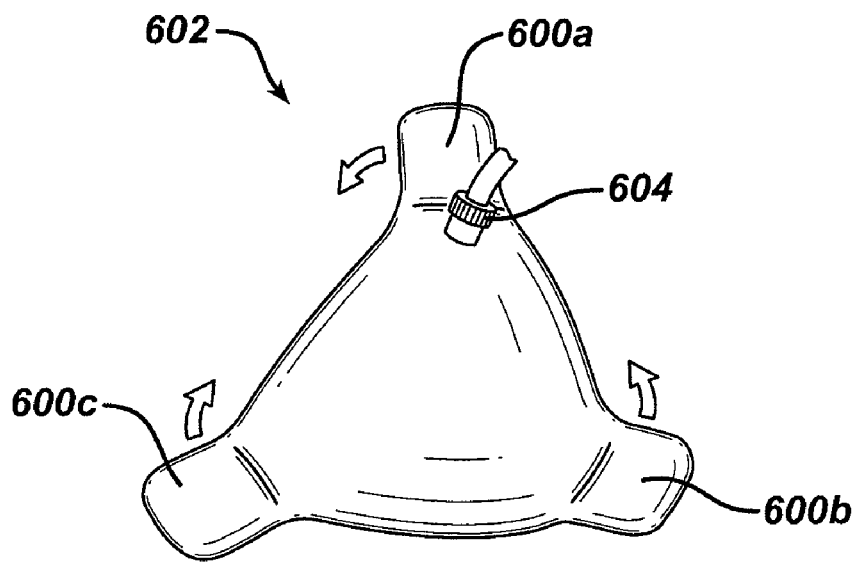
FIG. 6 is a schematic diagram of yet another embodiment of a retractor having an internal cavity and tabs.
Figure 7:
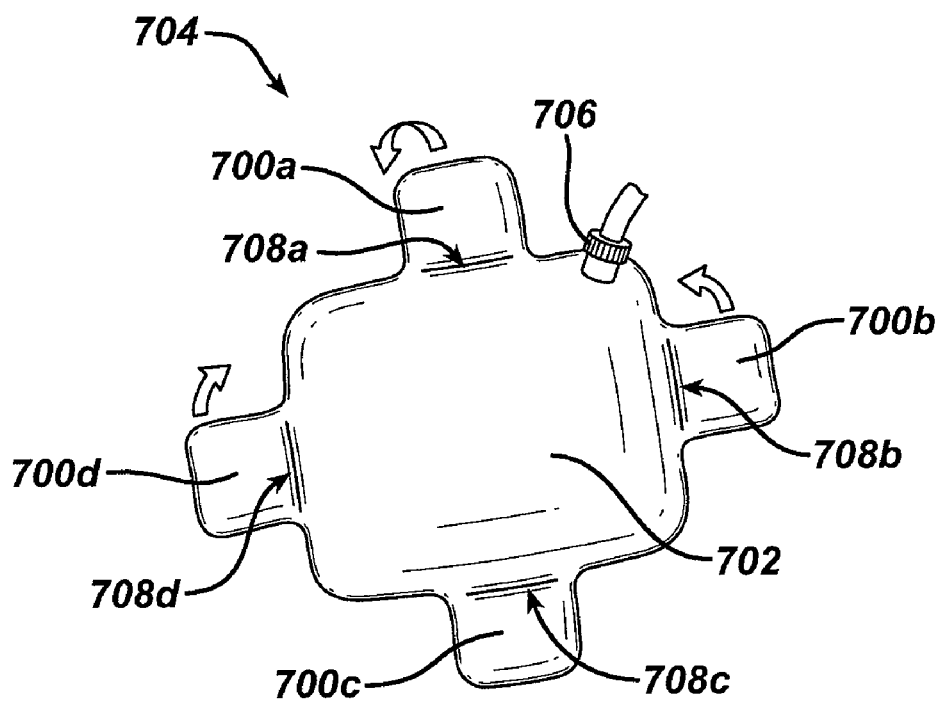
FIG. 7 is a schematic diagram of still another embodiment of a retractor having an internal cavity and tabs.

The tabs 408a, 408b can have any configuration on the retractor 400. In the illustrated embodiment, the tabs 408a, 408b extend linearly from corners of the central body 406, forming a U-shaped retractor body 402. The tabs 408a, 408b, however, can be attached to the retractor body 402 in any configuration. For example, as shown in FIG. 5, tabs 500a, 500b, 500c, 500d can extend diagonally from each corner of a retractor 502. The retractor 502 also includes a valve 504 located in a non-corner position along its perimeter. Tabs 600a, 600b, 600c can also extend from corners of a substantially triangular retractor 602 that has a valve 604 located on its top surface, as shown in FIG. 6. For another example, illustrated in FIG. 7, tabs 700a, 700b, 700c, 700d can be located one each per side of central body 702 of a retractor 704 while a valve 706 is mated to one of the retractor's corners. Junctions between the tabs 700a, 700b, 700c, 700d and the central body 702 in this example include weakened regions 708a, 708b, 708c, 708d.

Figure 8:
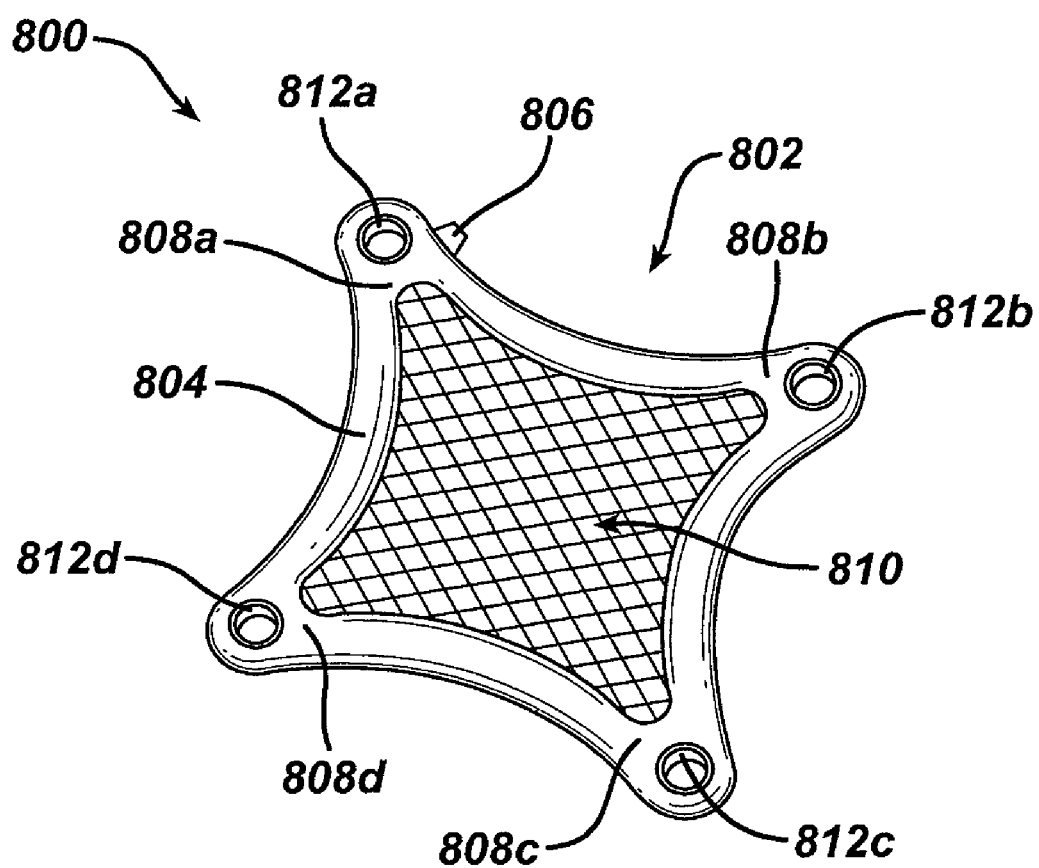
FIG. 8 is a schematic diagram of an embodiment of a retractor having an internal cavity around its perimeter.

FIG. 8 illustrates another embodiment of a retractor 800 that includes a retractor body 802 that can hold tissue during a surgical procedure. The retractor body 802 includes an internal cavity extending around a perimeter 804 of the retractor body 802 that can be of any size and extend any distance from an edge of the retractor body 802 toward a center of the retractor body 802. The retractor 800 also includes a valve 806 which, in an exemplary embodiment is coupled to one of four corners 808a, 808b, 808c, 808d of the retractor body 802, although it can be at any location on the retractor body 802. The retractor body 802, the internal cavity, and the valve 806 are similar to those described with reference to similarly named elements discussed above. Although the retractor 800 is shown in FIG. 8 to be substantially rectangular, it is understood that it can be a variety of alternative shapes.

The retractor body 802 also includes an internal fabric 810 disposed within a central opening defined by the internal cavity around the perimeter 804. The internal fabric 810 can be made from any biocompatible material appropriate for use in a body (discussed above), the same or different material from the perimeter 804. The internal fabric 810 is typically a more flexible material (e.g., braided mesh fabric) than the rest of the retractor body 802 to provide increased flexibility to the retractor 800. Braided mesh is a useful material for the internal fabric 810 because tissue is generally less likely to stick or snag on braided mesh than on other materials. In one embodiment, the internal fabric 810 is fluid permeable.

The retractor body 802 also includes grasping elements 812a, 812b, 812c, 812d. The grasping elements 812a, 812b, 812c, 812d, shown here as grommets, can be coupled to each of the retractor body's four corners 808a, 808b, 808c, 808d, although the retractor 800 could include any number of grasping elements at any location on the retractor body 802. Once inside the body, the retractor 800 can be manipulated to receive, hold, move, and release tissue by grasping and pulling (including tightening and slackening) one or more elements, such as the grasping elements 812a, 812b, 812c, 812d. Additionally, the retractor 800, and any tissue it supports, can be held in a substantially fixed position within the body by anchoring one or more of the grasping elements 812a, 812b, 812c, 812d to a port, as further described below.

The grasping elements 812a, 812b, 812c, 812d attached to the retractor body 802 can also have any structure. For example, the grasping elements 812a, 812b, 812c, 812d can include any combination of grommets, clips, wraparound ties/loops, hooks, magnetic clasps, clamps, holes formed in the retractor body 802, and other similar structures. The grasping elements 812a, 812b, 812c, 812d can be formed of any biocompatible material appropriate for use in a body (discussed above). Each of the grasping elements 812a, 812b, 812c, 812d can be made from the same material, but one or more of the grasping elements 812a, 812b, 812c, 812d can be made from a material different from one or more of the other grasping elements 812a, 812b, 812c, 812d. The grasping elements 812a, 812b, 812c, 812d can be made from a non-elastic material, but they can be flexible or rigid.

The grasping elements 812a, 812b, 812c, 812d can have any shape, such as elliptical (including circular). The grasping elements 812a, 812b, 812c, 812d can also have any length and width. Preferably, the grasping elements 812a, 812b, 812c, 812d are of a shape compatible to fit around or otherwise couple to commercially available trocars, as further discussed below, thereby allowing the grasping elements 812a, 812b, 812c, 812d to be manipulated around the trocars when receiving, releasing, supporting, or moving tissue in the retractor 800.

As indicated above, the grasping elements 812a, 812b, 812c, 812d can be used to anchor the retractor 800 in a substantially fixed position. The grasping elements 812a, 812b, 812c, 812d can also be used for pulling the retractor 800 when introducing the retractor 800 into a body cavity, when receiving tissue in or releasing tissue from the retractor 800, and when moving tissue held in the retractor 800. Any number of grasping elements 812a, 812b, 812c, 812d can be coupled to the retractor body 802 in any configuration, and the grasping elements 812a, 812b, 812c, 812d can be coupled to the retractor body 802 at any point or points along the perimeter 804 and/or on the internal fabric 810. Preferably, there are at least two grasping elements 812a, 812b, 812c, 812d coupled to the retractor 800 to provide adequate tension when using the grasping elements 812a, 812b, 812c, 812d in moving or securing the retractor 800. The grasping elements 812a, 812b, 812c, 812d can be mated to the retractor body 802, or they can be integrally formed with the retractor body 802. For example, FIG. 8 illustrates four individual grasping elements 812a, 812b, 812c, 812d, each mated to the retractor body 802 in the perimeter 804 at the corners 808a, 808b, 808c, 808d with the retractor's internal cavity surrounding the grasping elements 812a, 812b, 812c, 812d. For another example, the grasping elements 812a, 812b, 812c, 812d could include loops of fabric extending from one or more places along the retractor body's perimeter 804. The grasping elements 812a, 812b, 812c, 812d are preferably permanently coupled to the retractor body 802, but one or more of the grasping elements 812a, 812b, 812c, 812d can be removable. Further information on grasping elements coupled to a retractor can be obtained from U.S. patent application Ser. No. 11/944,806, entitled "Tissue Retractors" by Patrick Minnelli, filed Nov. 26, 2007, and hereby incorporated by reference in its entirety.

Figure 9:
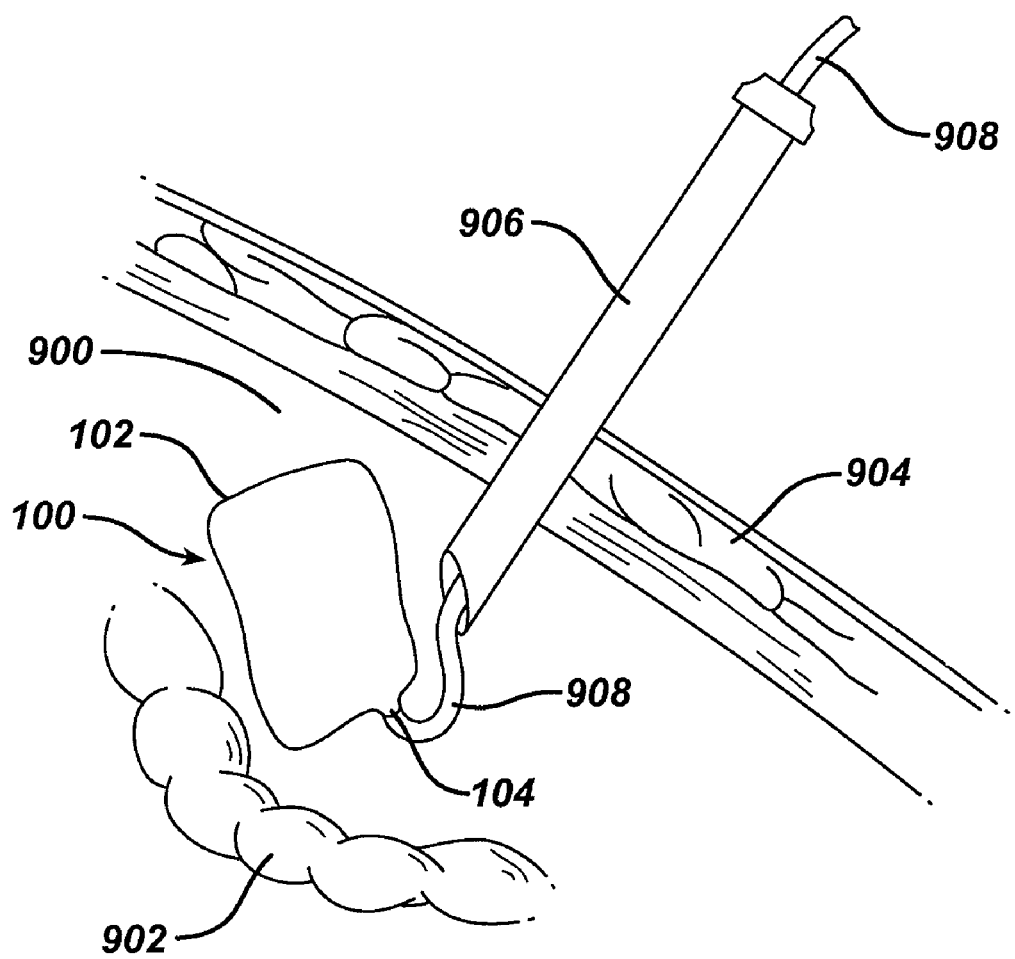
FIG. 9 is a perspective view of the retractor of FIG. 1 shown disposed in a body cavity.

FIG. 9 illustrates the retractor 100 of FIG. 1 in use in a body cavity 900 (e.g., the abdomen). With the retractor 100 disposed in the body cavity 900, the retractor 100 can be manipulated to position the retractor 100 where it can hold and/or move a tissue 902. Although the retractor 100 of FIG. 1 is shown, the illustrated methods can be performed using any retractor disclosed herein or known in the art.

The retractor 100 can be inserted into the body cavity 900 in a variety of ways, such as through a port, such as an incision (e.g., a HALS access port) made in a body wall 904 (e.g., the abdominal wall) or through an access device (e.g., a trocar 906, as shown, a cannula, etc.) extending from outside the body wall 904. Although the trocar 906 is shown in a perpendicular position relative to the body wall 904, the trocar 906 can be at any angle and may move horizontally and/or vertically during use. The retractor 100 can be introduced into the body cavity 900 in a closed position, in which the retractor 100 can be folded, rolled, or otherwise compressed in size and fit through a port, but once partially or fully disposed in the body cavity 900, the retractor 100 can be moved to an open position, in which the retractor body 102 can support tissue. The retractor 100 is typically disposed in the body cavity 900 in a pliable state as shown in FIG. 9, although it can be introduced in a rigid state.

A tube 908 capable of communicating fluid in and/or out of the retractor's internal cavity 200 (see FIGS. 2 and 3) can be coupled to the retractor's valve 104, as illustrated, either before or after the retractor 100 has been disposed in the body cavity 900. The tube 908 is shown extending through the trocar 906 used to introduce the retractor 100 into the body cavity 900, but the tube 908 can extend through any port.

Once the retractor 100 has been introduced into the body cavity 900, a surgeon can position the retractor 100 to hold the tissue 902. The retractor 100 can hold any amount of the tissue 902 and in any or all portions of the retractor 100. The tissue 902 can include more than one type of tissue, thereby allowing one retractor to simultaneously move multiple types of tissue. The tissue 902 can be held in more than one retractor, although only one retractor 100 is shown in the illustrated embodiment.

Figure 10:
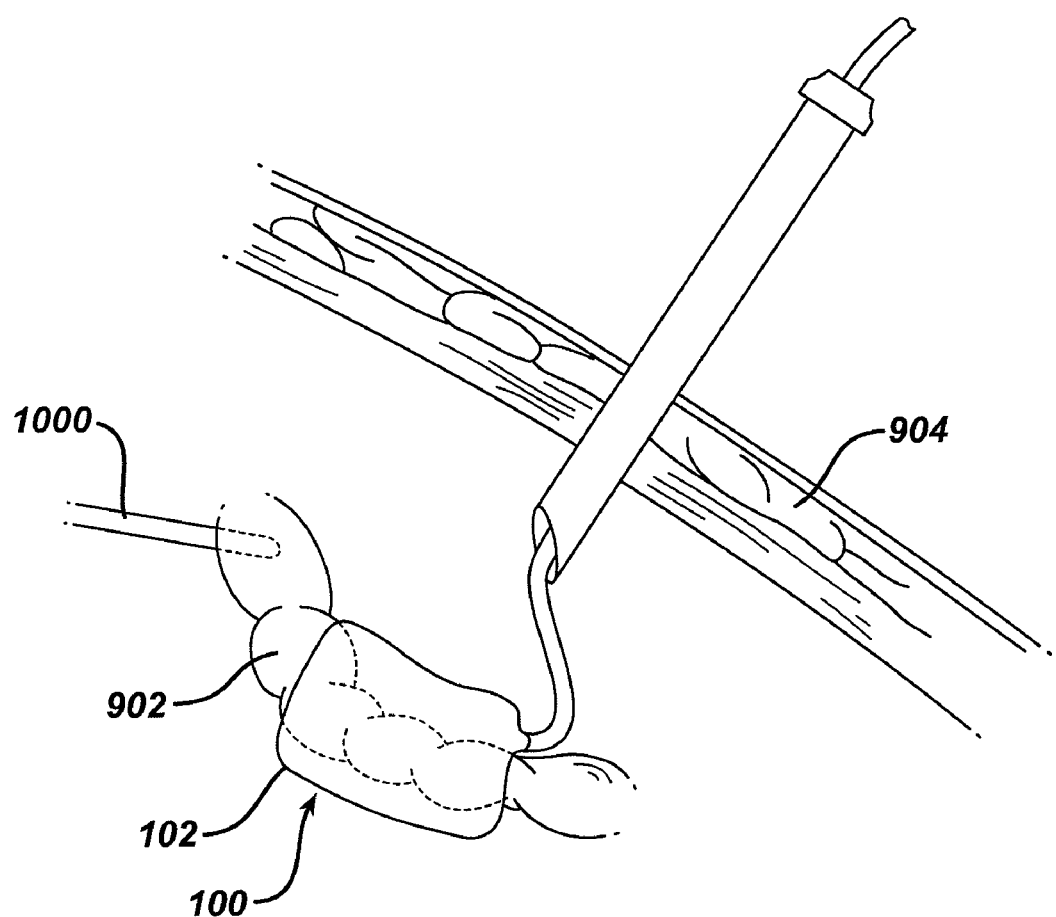
FIG. 10 is a perspective view of the retractor of FIG. 9 showing tissue positioned relative to the retractor.

Referring to FIG. 10, the tissue 902 is shown positioned with respect to the retractor 100 such that the retractor body 102 supports the tissue 902. The tissue 902 can be positioned with respect to the retractor 100 in a variety of ways that can be performed alone or in any combination. For example, positioning the tissue 902 with respect to the retractor 100 can include manipulating the retractor body 102 with at least one grasping device. Examples of grasping devices include fingers, hands, and any instrument safe for surgical use and capable of grasping the tissue 902 and/or the retractor 100 such as forceps, rods, a spatula 1000 as shown, and other similar instruments. The grasping device 1000 can grip, push, pull, or otherwise move the tissue 902 and/or the retractor 100 to position the tissue 902 with respect to the retractor 100 or to position the retractor 100 in a location proximate to the tissue 712. Gravity can move the tissue 902 from the proximate location to a position such that the tissue 902 can be supported by the retractor body 102.

In another example, positioning the tissue 902 can include manipulating one or more grasping elements coupled to the retractor 100 to move the retractor 100 around the tissue 902 (e.g., using a grasping device). One or more of the grasping elements can be simultaneously or sequentially pulled to position the tissue 902 with respect to the retractor 100 or to position the retractor 100 in a location proximate to the tissue 902. As yet another example, one or more tabs coupled to the retractor body 102 can be simultaneously or sequentially folded (e.g., using a grasping device) to place the tissue 902 with respect to the retractor 100 or to place the retractor 100 around the tissue 902.

Figure 11:
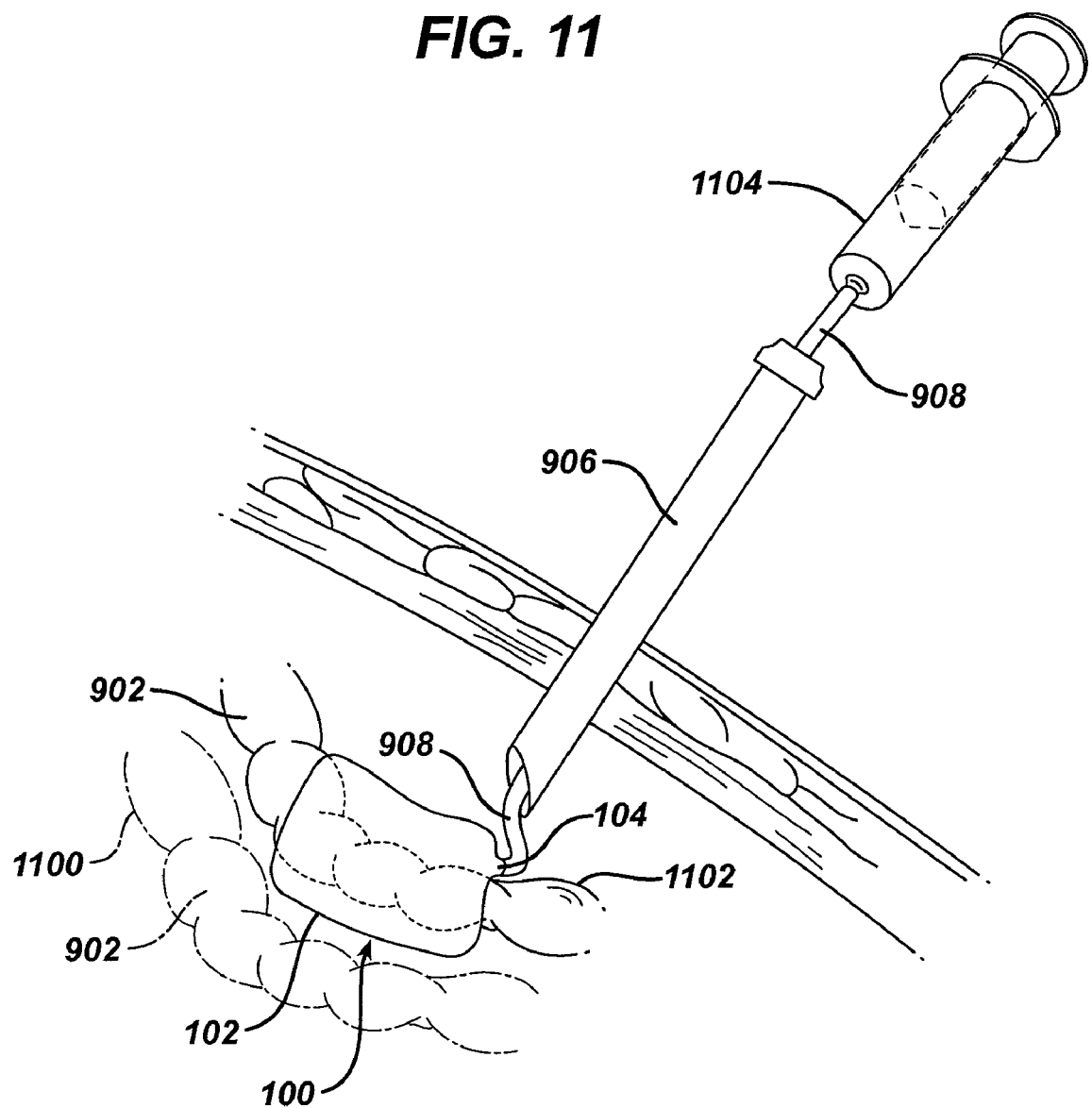
FIG. 11 is a perspective view of the retractor of FIG. 9 showing the retractor manipulated to move the tissue.

Once the retractor 100 supports a desired amount of the tissue 902, the retractor 100 can be manipulated to move the tissue 902. As shown in FIG. 11, the retractor 100 has been manipulated to move the tissue 902 supported by the retractor body 102. The tissue 902 has been moved from a first position 1100 (the tissue 902 shown with dotted lines) to a second position 1102 (the tissue 902 shown with solid lines). The two positions 1100, 1102 are examples; the tissue 902 can be moved in any direction and between any number of positions during any one surgical procedure.

The tissue 902 can be moved while supported by the retractor 100 in a variety of ways that can be performed alone or in combination. For example, at least one grasping element and/or tab coupled to the retractor 100 can be manipulated. In another example, a grasping device can manipulate the retractor 100.

Once moved to a desired configuration such as the second position 1002, the retractor 100 can be fixed to anchor the retractor 100 and thus the tissue 902 in the second position 1002. Fixing the retractor 100 can be accomplished by, for example, configuring the retractor body 102 from a pliable state to a substantially rigid state, shown in FIG. 11. Fixed in the second position 1002, the tissue 902 can be held in that particular position with minimal or no human interaction during a surgical procedure. The retractor 100 can still be easily adjusted, e.g., by moving the substantially rigid retractor body 102, manipulating grasping elements, opening the valve 104 to introduce and/or evacuate fluid from the internal cavity 200, etc.

Configuring the retractor body 102 in a substantially rigid state can be accomplished in a variety of ways. For example, a pump device 1104 (e.g., a surgical syringe) coupled to the tube 908 (or, in some embodiments, coupled directly to the valve 104) can apply suction to the internal cavity 200 when the valve 104 is in an open position. The suction can draw a vacuum inside the internal cavity 200 by evacuating at least a portion of the fluid 204 such that the granules 202 compact together in the positioned shape of the retractor body 102. In other words, the ability of the granules 202 to move is constrained and a mass is created within the internal cavity 200 that becomes more rigid as more of the fluid 204 is evacuated. Although the granules 202 are shown having the same spherical shapes in the pliable state of FIG. 2 and the substantially rigid state of FIG. 3, one or more of the granules 202 may themselves compress due to the vacuum force, e.g., have a smaller diameter and/or a different shape. Conversely, introducing fluid into the internal cavity 200 through the tube 908 (using the pump device 1104 or another fluid introduction device) can de-compact the granules 202 and make the retractor body 102 more pliable as more fluid is introduced to the internal cavity 200. The retractor body 102 can be manipulated with a grasping device while the pump device 1104 evacuates the fluid 204 from and/or introduces fluid to the internal cavity 202, thereby allowing the retractor 100, and thus the tissue 902, to be continually positioned to reach a desired conformation where the retractor 100 can hold the tissue 902 in a substantially fixed position. When a desired amount of the fluid 204 has been evacuated from (and/or introduced to) the internal cavity 200, the valve 104 can be closed, thereby putting the internal cavity 200 into an equilibrium state. In the case of fluid evacuation, the equilibrium state is a substantially rigid state while in the case of fluid introduction, it is a pliable state.

Figure 12:
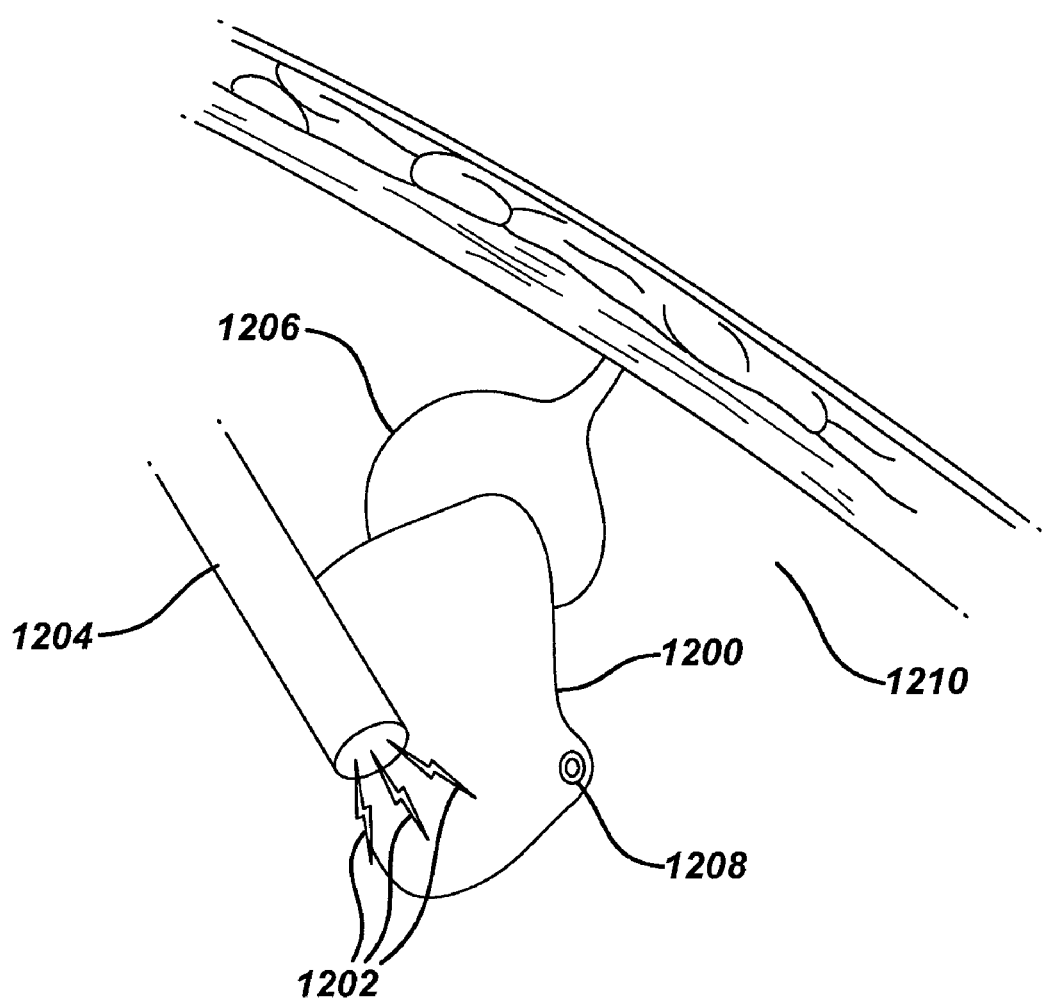
FIG. 12 is a perspective view of a retractor disposed in a body cavity and being manipulated to move tissue.

In other embodiments, illustrated in FIG. 12, configuring a retractor 1200 in a substantially rigid state can be accomplished by applying a magnetic field 1202 to the retractor 1200 using a magnetic device 1204. The retractor 1200 includes an internal cavity filled with fluid, similar to the retractor 102, the internal cavity 200, and the fluid 204 of FIGS. 1-3. However, the retractor 1200 typically does not include granules disposed in its internal cavity because the fluid disposed in the internal cavity can cause the retractor 1200 to have a substantially rigid state without the presence of any granules. The fluid within the retractor 1200 can include a viscous fluid (e.g., smart fluids and ferrofluids) responsive to the magnetic field 1202. When introduced to the magnetic field 1202, the fluid can increase in viscosity to the point of forming a substantially rigid mass. With the fluid and hence the retractor 1200 in such a substantially rigid state, the retractor 1200 can support a target tissue 1206 in a desired configuration. When the magnetic device 1204 and hence the magnetic field 1202 are removed, the fluid can decrease in viscosity and approximately return to its original, pliable state.

The retractor 1200 optionally includes a valve 1208 that can be coupled to one of its corners, although the valve 1208 can be located at any position on the retractor 1200. The valve 1208 can be set to an open position at any time so fluid can be introduced and/or evacuated from the retractor's internal cavity as described above. However, the valve 1208 typically remains in a closed position when the retractor 1200 is disposed in a body cavity 1210 as shown. The valve 104 is more typically set to an open position when the retractor 1200 is outside the body cavity 1210 so fluid in the internal cavity can be replaced because viscous fluid responsive to the magnetic field 1202 can decrease in effectiveness after repeated use.

Figure 13:
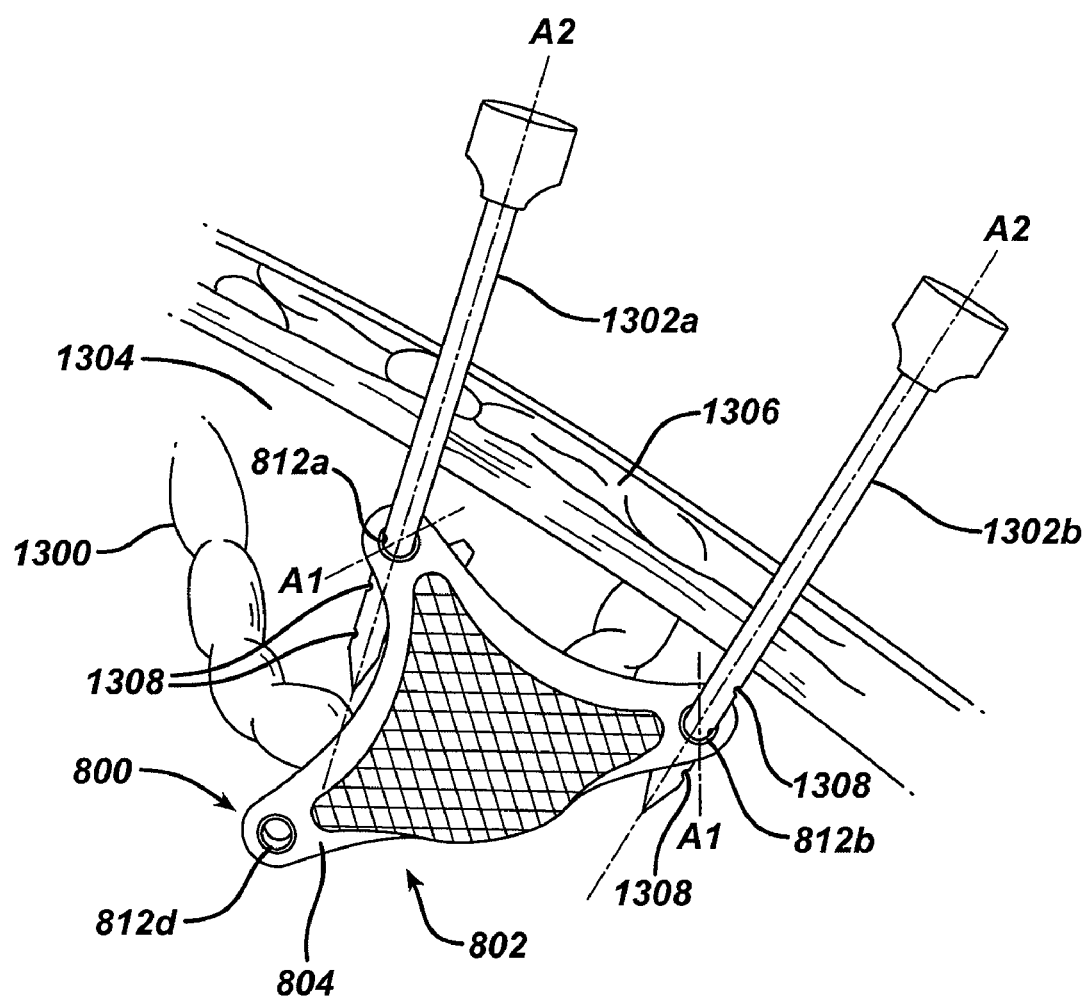
FIG. 13 is a perspective view of the retractor of FIG. 8 disposed in a body cavity and coupled to trocars.

In still other embodiments, illustrated in FIG. 13, one or more of the retractor's grasping elements 812a, 812b, 812c, 812d (see FIG. 8) can be manipulated to configure the retractor 800 and a target tissue 1300 in a substantially fixed position. First and second trocars 1302a, 1302b are shown in use with the retractor 800 in a body cavity 1304. Two trocars 1302a, 1302b are shown coupled to the retractor 800, but the retractor 800 can be coupled to any number of trocars. At least two trocars 1302a, 1302b are typically used to provide adequate tension when manipulating the retractor 800 to support tissue.

When the retractor 800 is in the body cavity 1304, one or more of the grasping elements 812a, 812b, 812c, 812d can be used to couple to the trocars 1302a, 1302b, typically using one grasping element per trocar. Thus, one or more of the grasping elements 812a, 812b, 812c, 812d can be manipulated to help position and/or secure the retractor 800 (and the tissue 1300) from one state to a desired state, e.g., a substantially fixed position.

The grasping elements 812a, 812b, 812c, 812d can couple to the trocars 1302a, 1302b in a variety of ways. Generally, the grasping elements 812a, 812b, 812c, 812d can each couple to an outside surface of an access port (such as the trocars 1302a, 1302b) inserted into the body cavity 1304. When one or more of the grasping elements 812a, 812b, 812c, 812d are coupled to an outside surface of a trocar, an inside surface of the trocar remains unobstructed to allow the trocar to receive an instrument (e.g., a pump device or a magnetic device) that can extend from outside a body wall 1306 to inside the body cavity 1304. Although only two grasping elements 812a, 812b are shown coupled to respective trocars 1302a, 1302b, the other grasping elements 812c, 812d can be coupled to the same or other trocars in a similar manner.

The grasping elements 812a, 812b each have a shape that allows them to be positioned around the trocars 1302a, 1302b such that longitudinal axes A1 of the grasping elements 812a, 812b are initially substantially parallel to longitudinal axes A2 of trocars 1302a, 1302b. With the axes A1, A2 so aligned, the grasping elements 812a, 812b can then be advanced proximally up their respective trocars 1302a, 1302b, e.g., in a direction from the body cavity 1304 toward the body wall 1306. A grasping device can be used to manipulate the grasping elements 812a, 812b on the trocars 1302a, 1302b.

Once the grasping elements 812a, 812b have been advanced on their respective trocars 1302a, 1302b to desirable positions, the grasping elements 812a, 812b can be simultaneously or sequentially released from the grasping device. Releasing the grasping elements 812a, 812b can cause them to rotate on their respective trocars 1302a, 1302b due to gravity and the weight of the retractor body 802. The longitudinal axes A1 of the grasping elements 812a, 812b can thereby be oriented at non-parallel and non-perpendicular angles to the longitudinal axes A2 of the trocars 1302a, 1302b, as shown in FIG. 13. Alternatively or in addition to relying on gravity, the grasping elements 812a, 812b can be manipulated (e.g., with a grasping device) to form the non-parallel and non-perpendicular angles. The grasping elements 812a, 812b can be at least in part formed from a material (e.g., a high friction elastomeric material) to increase their friction holding capability with respect to the trocars 1302a, 1302b. Alternatively or in addition, the grasping elements 812a, 812b can engage locking elements 1308 (e.g., shown as grooves formed in the outside surface of the trocars 1302a, 1302b) located on one or both of the trocars 1302a, 1302b to effectively lock the grasping elements 812a, 812b in position on the trocars 1302a, 1302b. One or both of the grasping elements 812a, 812b can include one or more locking support structures such as protrusions from or notches in their surfaces to help them engage the locking elements 1308.

Although the locking elements 1308 are shown as grooves in this illustrated embodiment, the locking elements 1308 can have any structure. For example, the locking elements 1308 can including any combination of grooves, hooks, magnets, loops, ties, protrusions, and other similar structures. The locking elements' structure typically matches the structure of the retractor's grasping element(s), e.g., using magnets to engage magnetic grasping elements, using protrusions to engage clamps, or using hooks to engage grommets or loops. Any number of locking elements 1308 can be coupled to the trocars 1302a, 1302b in any configuration, and the locking elements 1308 can include elements of any size at one or more locations along the trocar's length. The locking elements 1308 can also have any depth, width, and height. Additionally, each of the trocars 1302a, 1302b used with the retractor 800 can have any combination of the same or varying locking elements 1308.

The locking elements 1308 can be coupled to the trocars 1302a, 1302b using various techniques. For example, as shown in FIG. 13, the locking elements 1308 are formed in the trocars 1302a, 1302b. As another example, the locking elements 1308 can include a plurality grooves cut circumferentially around the outside surface of the trocars 1302a, 1302b. In other embodiments, the locking elements 1308 can be inlaid in or otherwise mated to the outer surface of the trocars 1302a, 1302b. The locking elements 1308 can be included as part of a trocar's manufacture or can be retrofitted to an existing trocar. The locking elements 1308 can be made from any type of material appropriate for use in a body, such as the material of the grasping elements 812a, 812b and the material of the trocars 1302a, 1302b. The locking elements 1308 are preferably made from a non-elastic material, but they can be flexible or rigid.

With the grasping elements 812a, 812b anchored to the trocars 1302a, 1302b in the locking elements 1308, the trocars 1302a, 1302b can still be otherwise used in a surgical procedure (as the trocars 1302a, 1302b also can before the grasping elements 812a, 812b couple to them). For example, an instrument, e.g., an endoscope, can be inserted through one or both of the trocars 1302a, 1302b to extend from outside the body wall 1306 to inside the body cavity 1304. For another example, another retractor could be inserted into the body cavity 1304 through one or both of the trocars 1302a, 1302b.

Once the retractor 800 has been introduced into the body cavity 1304, a surgeon can position the retractor 800 to hold the tissue 1300 as described above. The retractor 800 can be positioned to hold the tissue 1300, and the tissue 1300 can be supported by the retractor 800, before and/or after any number of the grasping elements 812a, 812b, 812c, 812d have been coupled to the trocars 1302a, 1302b. In one embodiment, at least one of the grasping elements 812a, 812b, 812c, 812d is coupled to at least one of the trocars 1302a, 1302b before any tissue is positioned in the retractor 800 to provide increased structural integrity to the retractor 800 during the retractor 800 and/or the tissue 1300 positioning. The retractor 800 can hold any amount of the tissue 1300 and in any or all portions of the retractor 800. The tissue 1300 can include more than one type of tissue, thereby allowing one retractor to simultaneously move multiple types of tissue. The tissue 1300 can be held in more than one retractor (which may or may not be joined together) although only one retractor 800 is shown in the illustrated embodiment.

The tissue 1300 is shown positioned in the retractor 800 such that the retractor 800 supports the tissue 1300 in a pliable state and alternatively in a substantially rigid state as described above. The tissue 1300 can be positioned in the retractor 800 in a variety of ways that can be performed alone or in any combination. For example, positioning the tissue 1300 in the retractor 800 can include manipulating the internal cavity around the retractor's perimeter 804 and/or the internal area 810 to move the retractor 800 around the tissue 1300. As another example, one or more of the grasping elements 812a, 812b can be adjusted vertically between any number of the locking elements 1308. One or more of the corners 808a, 808b, 808c, 808d and/or other elements coupled to the retractor 800 can be simultaneously or sequentially pulled to position the tissue 1300 in the retractor 800 or to position the retractor 800 in a location proximate to the tissue 1300. As illustrated, one of the corners 808c includes a tab that has been folded to support the tissue 1300. Gravity can move the tissue 1300 from the proximate location to a position such that the tissue 1300 can be supported by the retractor 800.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new and/or used instrument(s) is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims.

What is claimed is:

1. A surgical retractor device, comprising:
    a tissue retractor formed of a flexible biocompatible material defining an internal cavity in a central portion of the tissue retractor;
    a plurality of granules disposed in the internal cavity; and
    a plurality of tabs extending from a central body of the internal cavity, each of the tabs having an aperture formed therethrough, each of the apertures being configured to have a surgical tool inserted therethrough,
    wherein the tissue retractor has a first state in which it is selectively conformable to a target tissue in a body cavity in a desired configuration and a second state in which it is substantially rigid and in a substantially fixed conformation.

2. The device of claim 1, further comprising a valve located on an outer surface of the tissue retractor, the valve being in fluid communication with the internal cavity such that the valve can selectively allow passage of fluid therethrough.

3. The device of claim 2, wherein the tissue retractor is configured from the first state to the second state by removing fluid from within the internal cavity.

4. The device of claim 1, wherein the granules are composed of a biocompatible material.

5. The device of claim 1, further comprising at least one conduit in fluid communication with the internal cavity such that fluid can be removed from the internal cavity through the at least one conduit.

6. The device of claim 5, wherein the at least one conduit is detachable from the tissue retractor.

7. The device of claim 5, further comprising a valve in fluid communication with the internal cavity and configured to be coupled to the at least one conduit such that when the valve is coupled to the at least one conduit and the valve is in an open position, the at least one conduit is in fluid communication with the internal cavity.

8. The device of claim 1, wherein a weakened region is at a junction between each of the tabs and the central body, each of the tabs being configured to be folded at its respective weakened region relative to the central body.

9. The device of claim 1, wherein the internal cavity extends to a perimeter of the tissue retractor.

10. A surgical retractor device, comprising:
a biocompatible retractor body having an internal cavity, a plurality of tabs extending from a central body of the internal cavity, and the retractor body being configured to have a default non-rigid state and to be disposed in a body cavity, wherein the internal cavity extends around at least a portion of a perimeter of the retractor body, and the retractor body includes a flexible fabric disposed within the perimeter of the retractor body; and
constrictable material disposed in the internal cavity, wherein constricting the material causes the retractor body to be configured in a rigid state in which the retractor body is effective to support tissue in a body cavity in a selected substantially fixed position,
wherein each of the tabs has an aperture formed therethrough, each of the apertures being configured to have a surgical tool inserted therethrough.

11. The device of claim 10, wherein the material includes biocompatible granules.

12. The device of claim 10, further comprising a valve on the outside surface of the retractor body and coupled to the internal cavity, wherein the valve is adapted to allow fluid to be removed from the internal cavity, thereby causing the retractor body to change to the rigid state.

13. The device of claim 10, wherein the material includes a magnetic fluid configured to constrict when introduced to a magnetic field and configured to deconstrict when the magnetic field is removed.

14. A surgical method, comprising:
inserting a conformable tissue retractor into a body cavity in a first orientation, wherein the retractor has a central internal cavity comprising a plurality of granules, a plurality of tabs extending from the central internal cavity, each of the tabs having an aperture formed therethrough, each of the apertures being configured to have a surgical tool inserted therethrough;
positioning tissue with respect to the tissue retractor in a desired conformation that is different than the first orientation such that the tissue retractor supports a target tissue; and
evacuating a fluid from within the internal cavity such that the granules compact together to maintain the tissue retractor in the desired conformation such that it is able to hold the target tissue in a substantially fixed position.

15. The method of claim 14, wherein the step of evacuating a fluid involves applying a vacuum force to withdraw fluid from within the internal cavity.

16. The method of claim 15, further comprising removing the vacuum force and allowing fluid to re-enter the internal cavity to enable the target tissue to be released from the substantially fixed position.

17. The method of claim 16, wherein the step of removing the vacuum force involves opening a valve on the tissue retractor and in fluid communication with the internal cavity.

18. A surgical method, comprising:
introducing a pliable retractor into a body cavity in a conformable configuration in which the retractor is in a non-rigid state;
changing the retractor from the conformable configuration to a non-conformable configuration in which the retractor is in a rigid state and is in a desired orientation with respect to a target tissue such that the retractor is effective to support tissue in the body cavity in a substantially fixed position, the changing causing at least a subset of a plurality of granules disposed in the retractor to change at least one of a diameter and a shape; and
decompressing the plurality of granules disposed in an internal cavity of the retractor such that the retractor can change from the rigid state to the non-rigid state, the decompressing causing at least the subset of the plurality of granules disposed in the retractor to change in the at least one of the diameter and the shape, a plurality of tabs extending from a central body of the internal cavity, each of the tabs having an aperture formed therethrough, each of the apertures being configured to have a surgical tool inserted therethrough.

19. The method of claim 18, further comprising positioning the retractor in the body cavity such that the retractor supports tissue before configuring the retractor in the rigid state.

20. The method of claim 18, wherein the step of configuring the retractor involves introducing a vacuum to the internal cavity.

21. The method of claim 18, wherein the step of decompressing material involves removing a vacuum from the internal cavity.

* * * * *